United States Patent
Flexman et al.

(10) Patent No.: US 11,836,863 B2
(45) Date of Patent: Dec. 5, 2023

(54) AUGMENTED REALITY TRIGGERING OF DEVICES

(71) Applicant: KONINKLIJKE PHILIPS N.V., Eindhoven (NL)

(72) Inventors: Molly Lara Flexman, Melrose, MA (US); Atul Gupta, Bala Cynwyd, PA (US); Ashish Panse, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 244 days.

(21) Appl. No.: 16/762,155

(22) PCT Filed: Nov. 3, 2018

(86) PCT No.: PCT/EP2018/080071
§ 371 (c)(1),
(2) Date: May 7, 2020

(87) PCT Pub. No.: WO2019/091875
PCT Pub. Date: May 16, 2019

(65) Prior Publication Data
US 2020/0302694 A1 Sep. 24, 2020

Related U.S. Application Data

(60) Provisional application No. 62/582,478, filed on Nov. 7, 2017.

(51) Int. Cl.
G06T 19/00 (2011.01)
A61B 90/00 (2016.01)
(Continued)

(52) U.S. Cl.
CPC ............ *G06T 19/006* (2013.01); *A61B 90/36* (2016.02); *A61B 90/90* (2016.02); *G06F 3/011* (2013.01);
(Continued)

(58) Field of Classification Search
None
See application file for complete search history.

(56) References Cited

U.S. PATENT DOCUMENTS 10,636,323 B2 4/2020 Buras
2006/0258938 A1 11/2006 Hoffman
(Continued)

FOREIGN PATENT DOCUMENTS

JP 2004041778 A 2/2004
JP 2014226341 A 12/2014
(Continued)

OTHER PUBLICATIONS

Wang et al., "Augmented Reality Navigation With Automatic Marker-Free Image Registration Using 3-D Image Overlay for Dental Surgery", 2014. (Year: 2014).*
(Continued)

*Primary Examiner* — Nicholas R Wilson

(57) ABSTRACT

An augmented reality trigger system (10) comprising a primary augmented reality device (30) and a trigger action controller (40) for implementing an augmented reality trigger method based on a medical tool (20) and/or a tool identifier (21) 5 associated with the medical tool (20). In operation, the primary augmented reality device (30) generates a camera image of the real world, which may or may not at any time include the medical tool (20) and/or the tool identifier (21). The trigger action controller (40) recognizes a generation by the primary augmented reality device (30) of the camera image of the real world including the medical (Continued)

tool (20) and/or the tool 10 identifier (21) and in response to such recognition, triggers a medical procedure action by the primary augmented reality device (30) and/or a medical device (50) in support of a medical procedure involving the medical tool (20).

19 Claims, 7 Drawing Sheets

(51) Int. Cl.
| | |
|---|---|
| *A61B 90/90* | (2016.01) |
| *G06F 3/01* | (2006.01) |
| *G06T 7/60* | (2017.01) |
| *G06V 20/20* | (2022.01) |
| *A61F 2/24* | (2006.01) |
| *A61F 2/95* | (2013.01) |
| *A61M 25/01* | (2006.01) |
| *A61M 25/09* | (2006.01) |

(52) U.S. Cl.
CPC ............... *G06T 7/60* (2013.01); *G06V 20/20* (2022.01); *A61B 2090/365* (2016.02); *A61F 2/2427* (2013.01); *A61F 2/95* (2013.01); *A61M 25/0113* (2013.01); *A61M 25/09041* (2013.01); *G06T 2200/24* (2013.01); *G06V 2201/034* (2022.01)

(56) References Cited

U.S. PATENT DOCUMENTS

| | | | |
|---|---|---|---|
| 2018/0092698 A1* | 4/2018 | Chopra | ................. A61B 90/39 |
| 2018/0168741 A1 | 6/2018 | Swayze | |
| 2018/0242920 A1 | 8/2018 | Hresko | |
| 2020/0268455 A1 | 8/2020 | Zheng | |

FOREIGN PATENT DOCUMENTS

| | | |
|---|---|---|
| JP | 2017513086 A | 5/2017 |
| WO | 2017165301 A1 | 9/2017 |

OTHER PUBLICATIONS

PCT/EP2018/080071 ISR & WO, Dec. 19, 2018 11 Page Document.

\* cited by examiner

AUGMENTED REALITY TRIGGERING OF DEVICES

CROSS-REFERENCE TO PRIOR APPLICATIONS

This application is the U.S. National Phase application under 35 U.S.C. § 371 of International Application No. PCT/EP2018/080071, filed on Nov. 3, 2018, which claims the benefit of U.S. Provisional Patent Application No. 62/582,478 filed on Nov. 7, 2017. These applications are hereby incorporated by reference herein.

FIELD OF THE INVENTION

The present disclosure generally relates to an utilization of augmented reality devices during a medical procedure. The present disclosure specifically relates to a recognition of a medical tool and/or a tool identifier by an augmented reality device for triggering an action by the augmented reality device, a medical device and/or an additional augmented reality device during the medical procedure.

BACKGROUND OF THE INVENTION

Interaction with medical imaging systems currently involves an operator of a medical imaging system being tasked with determining a next action or step. For example, currently there is often a close coupling between a medical tool (e.g., a guidewire, a catheter, a stent, intravascular ultrasound (IVUS) catheter, a valve, a drill, etc.) and a medical imaging system being utilized in a medical procedure whereby an operator may configure the medical imaging system based on the medical tool for facilitating imaging during the medical procedure. For example, an operator may customize various features of an ultrasound imaging system based on an IVUS catheter for facilitating various features of the ultrasound imaging system (e.g., a navigation feature) associated with imaging the IVUS catheter.

While the operator customizing the medical imaging system based on the medical tool is a small step within the entire scope of the medical procedure, the workflow of the medical procedure is still nonetheless interrupted by this small step.

SUMMARY OF THE INVENTION

Augmented reality (AR) generally refers to a device displaying a live image stream that is supplemented with additional computer-generated information. More particularly, the live image stream may be via the eye, cameras, smart phones, tables, etc., and is augmented via a display to the AR user via glasses, contact lenses, projections or on the live image stream device itself (e.g., smart phone, tablet, etc.). The inventions of the present disclosure are premised on an object recognition of a medical tool and/or a tool identifier serving as a trigger for a medical procedure action by the augmented reality device, a medical device and/or an additional augmented reality device to thereby minimize any interruption to the workflow of a medical procedure involving the medical tool.

One embodiment of the inventions of the present disclosure is an augmented reality trigger system for implementing an augmented reality trigger method based on a medical tool and/or a tool identifier associated with the medical tool. The augmented reality trigger system comprises a primary augmented reality device and a trigger action controller. In operation, the primary augmented reality device generates a camera image of a real world, which at any given time may or may not include the medical tool and/or the tool identifier. The trigger action controller is configured to recognize a generation by the primary augmented reality device of the camera image of the real world including the medical tool and/or the tool identifier, and further configured to trigger a medical procedure action by the primary augmented reality device and/or a medical device in response to a recognition by the trigger action controller of the generation by the primary augmented reality device of the camera image of the real world including the medical tool and/or the tool identifier.

The trigger action controller may be installed within the primary augmented reality device as a controller integrated or segregated from an augmented reality controller or an auxiliary controller of the primary augmented reality device, or alternatively may be installed in another device (e.g., the medical device, a workstation, or an additional augmented reality device) in communication with the primary augmented reality device to thereby receive the camera image of the real world.

In a second embodiment of the inventions of the present disclosure, the trigger action controller includes a medical tool recognition module configured to recognize the generation by the primary augmented reality device of the camera image of the real world including the medical tool and/or the tool identifier, and further includes a medical device trigger module configured to trigger the medical procedure action by the primary augmented reality device and/or the medical device in response to the recognition by the medical tool recognition module of the generation by the primary augmented reality device of the camera image of the real world including the medical tool and/or the tool identifier.

The medical tool recognition module may be installed within the primary augmented reality device as a module executable by the augmented reality controller or an auxiliary controller of the primary augmented reality device, or alternatively may be an executable module installed in another device (e.g., the medical device, a workstation, or an additional augmented reality device) in communication with the primary augmented reality device to thereby receive the camera image of the real world.

The medical device trigger module may also be installed within the primary augmented reality device as a module executable by the augmented reality main controller or an auxiliary controller of the primary augmented reality device, or alternatively may be an executable module installed in another device (e.g., the medical device, a workstation, or an additional augmented reality device) in communication the medical tool recognition module to receive a notification of a recognition by the medical tool recognition module of the generation by the primary augmented reality device of the camera image of the real world including the medical tool and/or the tool identifier.

In a third embodiment of the inventions of the present disclosure, the augmented reality trigger method comprises the trigger action controller recognizing a generation by the primary augmented reality device of the camera image of the real world including the medical tool and/or the tool identifier, and further comprises the trigger action controller triggering the medical procedure action by the primary augmented reality device and/or the medical device in response to the recognition by trigger action controller of the generation by the primary augmented reality device of the camera image of the real world including the medical tool and/or the tool identifier.

Again, the trigger action controller may be installed within the primary augmented reality device as a controller integrated or segregated from the augmented reality main controller or an auxiliary controller of the primary augmented reality device, or alternatively may be installed in another device (e.g., the medical device, a workstation, or an additional augmented reality device) in communication with the primary augmented reality device to thereby receive the camera image of the real world.

For purposes of describing and claiming the inventions of the present disclosure:

(1) the term "medical procedure" broadly encompasses all procedures, as known in the art of the present disclosure and hereinafter conceived, for an imaging, a diagnosis and/or a treatment of a patient anatomy;

(2) the term "medical tool" broadly encompasses all tools, as known in the art of the present disclosure, utilized during a medical procedure. Examples of a medical tool include, but are not limited to, a guidewire, a catheter (e.g., a IVUS catheter and a balloon catheter), a valve, a stent, an ultrasound transducer (TEE, TTE), a drill and an endoscope.

(3) the term "medical system" broadly encompasses all medical systems, as known in the art of the present disclosure and hereinafter conceived, for implementing one or more medical procedures. Examples of a medical system include, but are not limited to interventional x-ray systems (fixed systems, mobile systems, hybrid ORs), ultrasound systems, patient monitoring systems, contrast injection systems, diagnostic imaging systems (x-ray, CT, PET, MRI).

(4) the term "medical device" broadly encompasses all medical devices, as known in the art of the present disclosure and hereinafter conceived, incorporated within a medical system for controlling an operation (e.g., actuating, imaging, tracking, navigating, etc.) and/or being associated within an operation of medical tool(s). Examples of a medical device include, but are not limited to, an imaging apparatus (e.g., X-ray apparatus, an ultrasound apparatus, a computed tomography apparatus, a magnetic resonance imaging apparatus, etc.), a tracking apparatus (e.g., an electromagnetic tracking apparatus, an optical tracking apparatus, a shape sensing tracking apparatus, etc.), and a robot apparatus (e.g., a snake robot, a spherical RCM robot, etc.), and a monitoring apparatus (e.g., an electrocardiogram monitor).

(5) the term "augmented reality trigger method" broadly encompasses all medical procedures incorporating the inventive principles of the present disclosure directed to an object recognition of a medical tool and/or a tool identifier within a camera image of real world serving as a trigger for a medical procedure action by the augmented reality device, a medical device and/or an additional augmented reality device as exemplary described in the present disclosure;

(6) the term "augmented reality trigger system" broadly encompasses all medical systems incorporating the inventive principles of the present disclosure encompassing an object recognition of a medical tool and/or a tool identifier within a camera image of a real world serving as a trigger for a medical procedure action by the augmented reality device, a medical device and/or an additional augmented reality device as exemplary described in the present disclosure;

(7) the term "augmented reality device" broadly encompasses all devices, as known in the art of the present disclosure and hereinafter conceived, implementing an augmented reality overlaying virtual object(s) on a real world display based on a camera image of the real world. Examples of an augmented reality device include, but are not limited to augmented reality head-mounted displays (e.g., GOOGLE GLASS™ HOLOLENS™, MAGIC LEAP™, VUSIX™ and META™);

(8) the term "camera image" broadly encompasses a picture or a video of an image of a real world generated by a camera or an equivalent device incorporated as a component of an augmented reality device;

(9) the term "object recognition" broadly encompasses all techniques, as known in the art of the present disclosure and hereinafter conceived, for recognizing an object within a camera image;

(10) the phrase "triggering a medical procedure action" and tenses thereof broadly encompasses all techniques, as known in the art of the present disclosure and hereinafter conceived, for enabling and/or commanding an action in support of pre-operative step(s) and/or intra-operative step(s) of a medical procedure, particularly a configuration commanding, signal enabling/disabling (unmodulated and modulated) and/or a function calling of an augmented reality device or a medical device;

(11) the term "controller" broadly encompasses all structural configurations, as understood in the art of the present disclosure and as exemplary described in the present disclosure, of an application specific main board or an application specific integrated circuit for controlling an application of various inventive principles of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to an augmented reality device, a medical device and/or a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop, a laptop or a tablet;

(12) the descriptive labels for controllers described and claimed herein facilitate a distinction between controllers as described and claimed herein without specifying or implying any additional limitation to the term "controller";

(13) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application;

(14) the descriptive labels for application modules described and claimed herein facilitate a distinction between application modules as described and claimed herein without specifying or implying any additional limitation to the term "controller";

(15) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium; and

(16) the descriptive labels for signals/data/commands as described and claimed herein facilitate a distinction between signals/data/commands as described and claimed herein without specifying or implying any additional limitation to the terms "signal", "data" and "command".

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

Figure 1:
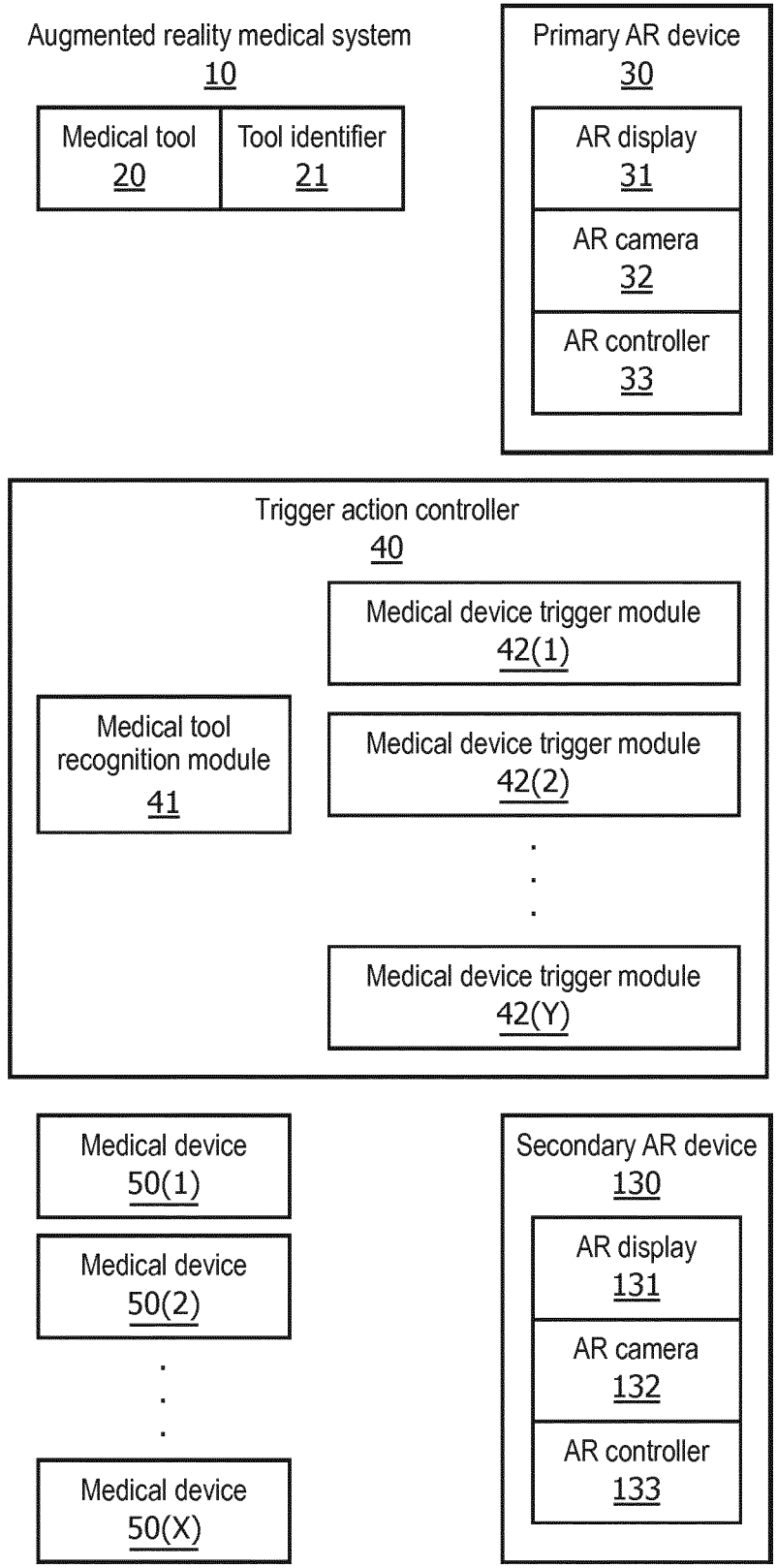
FIG. 1 illustrates an exemplary embodiment of an augmented reality trigger system in accordance with the inventive principles of the present disclosure.

To facilitate an understanding of the various inventions of the present disclosure, the following description of FIG. 1 teaches basic inventive principles associated with augmented reality trigger systems of the present disclosure. From this description, those having ordinary skill in the art will appreciate how to apply the inventive principles of the present disclosure for making and using additional embodiments of augmented reality trigger systems of the present disclosure.

Referring to FIG. 1, an augmented reality trigger system 10 employs a primary augmented reality (AR) device 30 and trigger action controller 40 for implementing an augmented reality trigger method of the present disclosure based on a medical tool 20 and/or a tool identifier 21. Generally, the augmented reality trigger method provides for a object recognition of medical tool 20 and/or a tool identifier 21 within a camera image of a real world serving as a trigger for a medical procedure action by primary AR device 30, one or more of an X number of a medical devices 50, X≥1 and/or a secondary augmented reality device 130 as will be further described in the present disclosure.

Still referring to FIG. 1, medical tool 20 (e.g., a guidewire, a catheter, a valve, a stent, etc.) is associated with a tool identifier 21 for facilitating a recognition of medical tool 20 by primary augmented device 30 within a camera image of a real world including medical tool 20 and/or tool identifier 21 as will be further exemplary described in the present disclosure.

In practice, tool identifier 21 may be associated with medical tool 20 in any manner suitable for a recognition of medical tool 20 via primary augmented device 30.

Figure 2A:
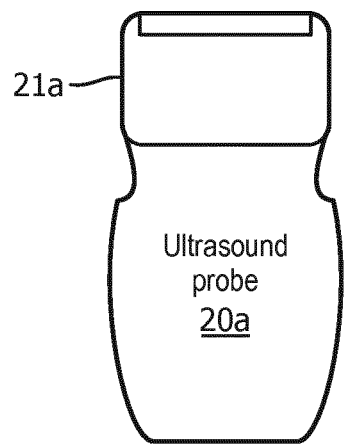
FIGS. 2A-2D illustrate exemplary embodiments of a tool identifier in accordance with the inventive principles of the present disclosure.

In one embodiment, tool identifier 21 may be embodied as a shape of a medical tool 20, such as, for example, a shape 21a of an ultrasound probe 20a as shown in FIG. 2A or a shape of a pre-formed catheter.

Figure 2B:
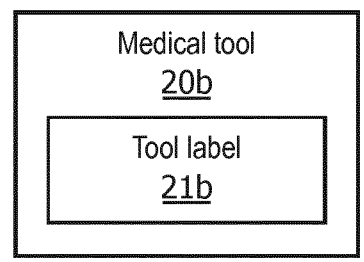

In a second embodiment, tool identifier 21 may be a tool label affixed onto a medical tool 20, such as, for example, a tool label 21b attached to a medical tool 20b as shown in FIG. 2B, and/or alternatively tool identifier 21 may be a tool label affixed onto a packaging/storage container of a medical tool 20. In practice, the tool label may be a standard commercial labeling or a user-generated labeling of a medical tool 20 or a packaging/storage container of the medical tool 20.

Figure 2C:
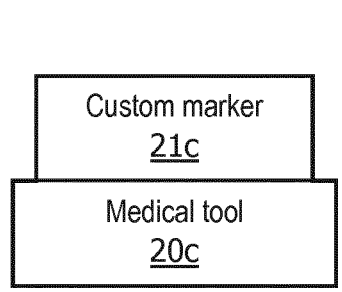

In a third embodiment, tool identifier 21 may be a custom marker attached to a medical tool 20, such as, for example, a customer marker 21c attached to a medical tool 20c as shown in FIG. 2C. In practice, a custom marker is a marker generated on behalf of the operators of system 10 for the purpose of identifying the medical tool 20.

Figure 2D:
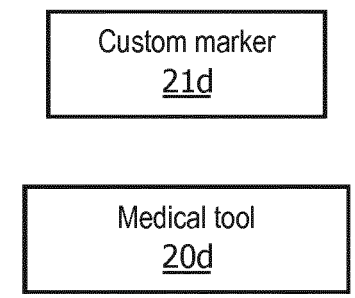

In a fourth embodiment, tool identifier 21 may a custom marker unattached to a medical tool 20, such as for example, a custom marker 21d unattached to a medical tool 20d as shown in FIG. 2D. For this embodiment, the customer marker may be a physical procedure card imprinted with a graphic and text indicating to activation setting of a medical tool 20 and/or operational setting of a medical device 51 for imaging, tracking or navigating medical tool 20 (e.g., geometry or x-ray settings or virtual screen layout settings to activate medical tool 20). More particularly, a stack of such physical procedure cards could be pre-printed for any individual case, and at an appropriate step of a medical procedure, a technologist may be guided through each subsequent step of the medical procedure by flipping through the stack of customized physical procedure cards, simply by looking at the marker on each card.

Referring back to FIG. 1, each medical device 50 is configured for controlling an operation (e.g., actuating, imaging, tracking, navigating) medical tool 20 and/or being associated with an operation of medical tool 20 as known in the art of the present disclosure.

In one embodiment, a medical device 50 may be an imaging apparatus (e.g., X-ray apparatus, an ultrasound apparatus, a computed tomography apparatus, a magnetic resonance imaging apparatus, etc.) for imaging, treating or monitoring medical tool 20 relative to a patient anatomy during a medical procedure.

In a second embodiment, a medical device 50 may be a tracking apparatus (e.g., an electromagnetic tracking apparatus, an optical tracking apparatus, a shape sensing tracking apparatus, etc.) for tracking a position of medical tool 20 relative to a patient anatomy during the medical procedure.

In a third embodiment, a medical device 50 may be a robot apparatus (e.g., a snake robot, a spherical RCM robot, etc.) for navigating medical tool 20 relative to a patient anatomy during the medical procedure.

In a fourth embodiment, a medical device 50 may be a monitoring apparatus (e.g., an electrocardiogram monitor) for monitoring one or more conditions of a patient.

Still referring to FIG. 1, primary augmented reality device 30 employs an augmented reality display 31, an augmented reality camera 32 and an augmented reality controller 33 as known in the art of the present disclosure. In practice, in accordance with one or more augmented reality applications, augmented reality controller 33 controls an operation of augmented reality camera 32 in generating a camera image of a real world as known in the art of the present disclosure and further controls a display by augmented reality display 31 of an augmentation of a live image stream via a display of a camera image of the real world generated augmented reality camera 32, operator vision of the real world or an image of the real world displayed by another device (e.g., smart phones, tables, etc.).

Similarly, secondary augmented reality device 130 employs an augmented reality display 131, an augmented reality camera 132 and an augmented reality controller 133 as known in the art of the present disclosure. In practice, augmented reality controller 133 controls an operation of augmented reality camera 132 in generating a camera image of a real world as known in the art of the present disclosure and further controls a display by augmented reality display 131 of an augmentation of a live image stream via a display of a camera image of the real world generated augmented reality camera 132, operator vision of the real world or an image of the real world displayed by another device (e.g., smart phones, tables, etc.).

Note augmented reality device 30 is designated in this present disclosure as primary and augmented reality device 30 is designated in this present disclosure as secondary only for purposes of distinguishing which AR device is utilized for an object recognition of medical tool 20 and/or tool identifier 21 within a camera image of a real world as will be further exemplary described in the present disclosure.

Still referring to FIG. 1, trigger action controller 40 employs a medical tool recognition module 41 and a Y number of medical device trigger modules 42, Y≥1. Generally, medical tool recognition module 41 is configured to recognize medical tool 20 and/or tool identifier 21 within a camera image of a real world generated by augmented reality camera 32 as will be further exemplary described in the present disclosure, and each medical device trigger module 42 is configured to trigger a medical procedure action by primary augmented reality device 30, one or more medical devices 50 and/or secondary augmented reality device in response a recognition by medical tool recognition module 41 of medical tool 20 and/or tool identifier 21 within a camera image of a real world generated by augmented reality camera 32 as will be further exemplary described in the present disclosure.

In one embodiment, trigger action controller 40 includes processor(s), memory, a user interface, a network interface, and a storage interconnected via one or more system buses.

Each processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage stores medical tool recognition module 41 and medical device trigger module(s) 42 in the form of executable software/firmware for implementing the various functions of trigger action controller 40 as further described in the present disclosure.

Figure 3A:
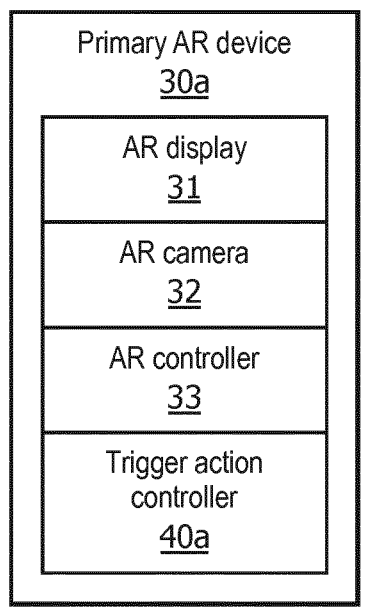
FIGS. 3A-3D illustrates exemplary embodiments of trigger action controller in accordance with the inventive principles of the present disclosure.
Figure 3B:
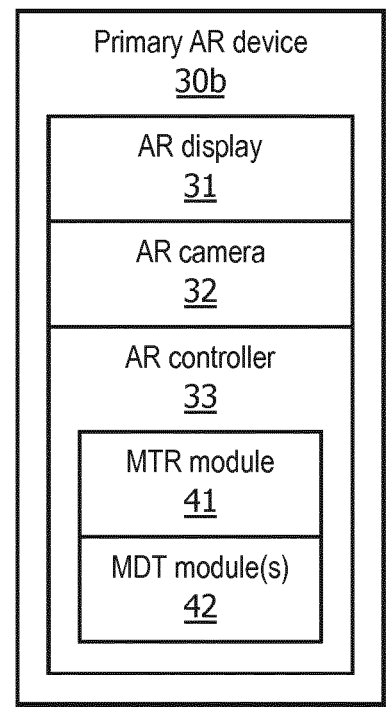

In practice, trigger action controller 40 may be installed within primary augmented reality device 30, such as, for example, an installation of trigger action controller 40*a* in a primary augmented reality device 30*a* as shown in FIG. 3A or a programming/installation of medical tool recognition (MTR) module 41 and medical device trigger (MDT) module(s) 42 in a primary augmented reality device 30*b* as shown in FIG. 3B.

Figure 3C:
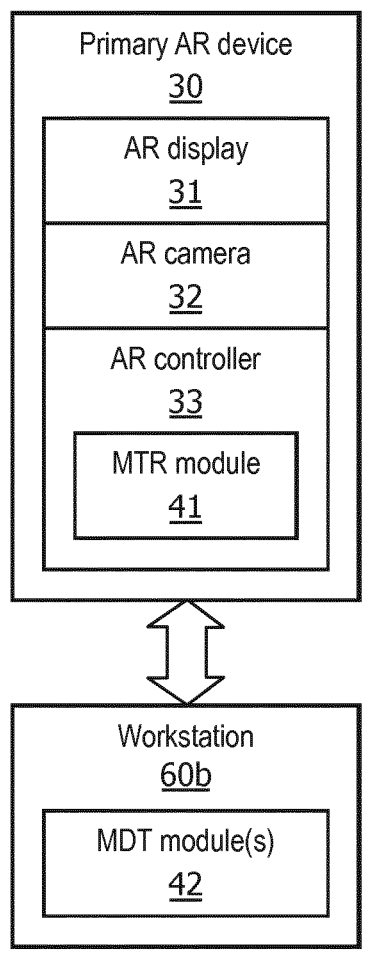
Figure 3D:
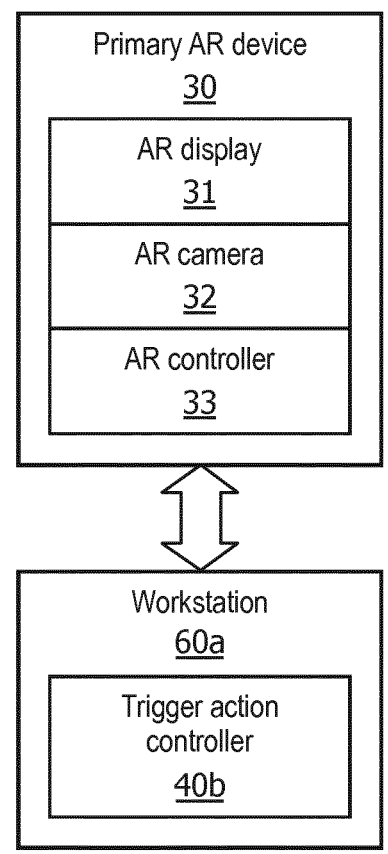

Alternatively, trigger action controller 40 may be partially or completely installed within a workstation, such as, for example, an installation of trigger action controller 40*b* in workstation 60*a* having a wired/wireless connection with primary augmented reality device 30 as shown in FIG. 3C, or a programming/installation of medical tool recognition (MTR) module 41 in a primary augmented reality device 30*b* and a programming/installation of medical device trigger (MDT) module(s) 42 in a workstation 60*b* as shown in FIG. 3D.

One or more medical device trigger (MDT) module(s) 42 may also concurrently or alternatively be programmed/installed within a medical device 50.

Figure 4:
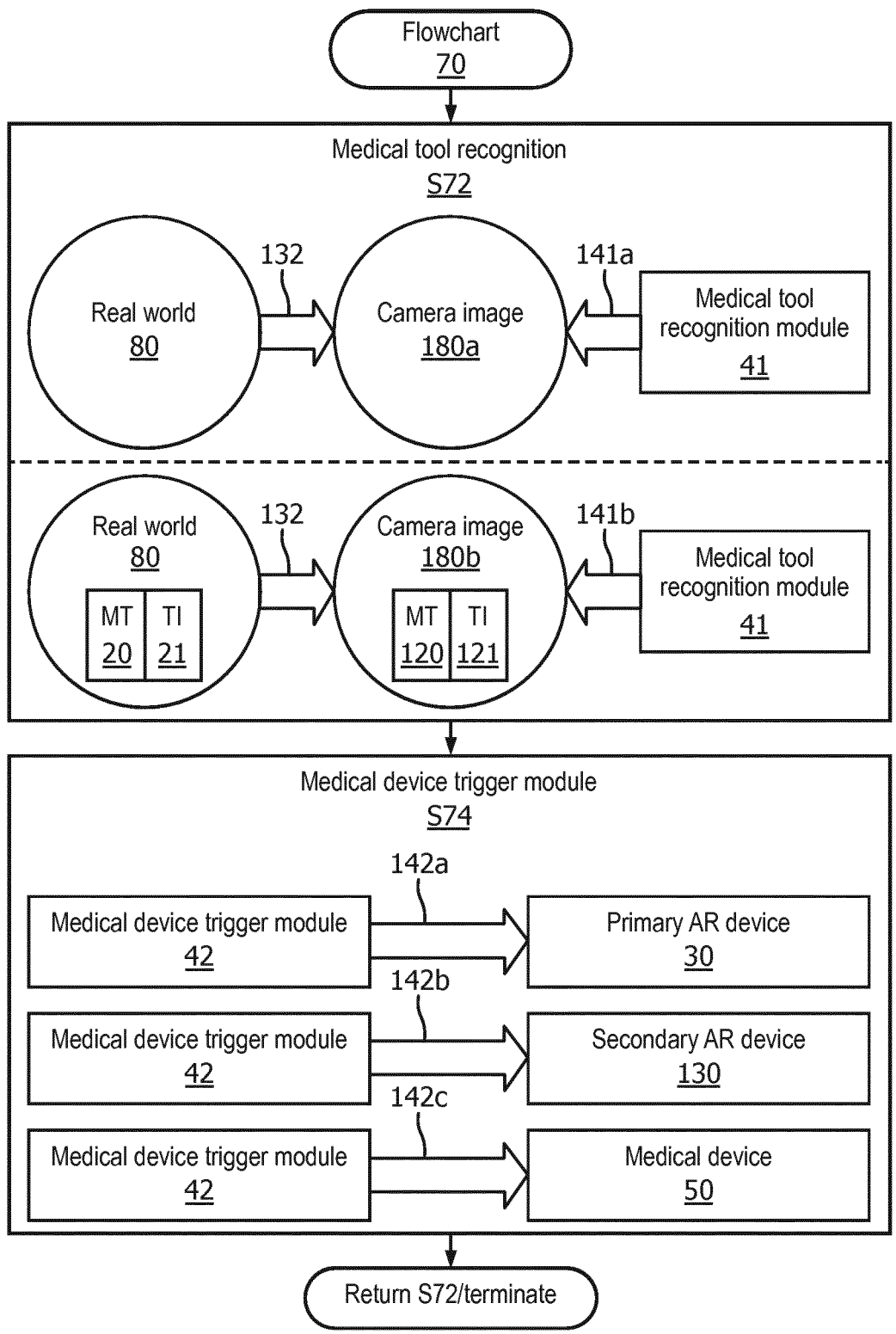
FIG. 4 illustrates a flowchart representative of an exemplary embodiment of an augmented reality trigger method in accordance with the inventive principles of the present disclosure.

To facilitate a further understanding of the various inventions of the present disclosure, the following description of FIG. 4 teaches basic inventive principles associated with augmented reality trigger methods of the present disclosure. From this description, those having ordinary skill in the art will appreciate how to apply the inventive principles of the present disclosure for making and using additional embodiments of augmented reality trigger methods of the present disclosure.

Referring to FIG. 4, a flowchart 70 is representative augmented reality trigger method of the present disclosure executable by medical tool recognition module 41 and medical device trigger module(s) 42 of FIG. 1.

Referring to FIGS. 1 and 4, a stage S72 of flowchart 70 encompasses AR camera 32 generating a feed 132 of a camera image 180 of a real world 80. At any given time, AR camera 32 may be generating feed 132 of a camera image 180a of real world 80 excluding medical tool 20 and tool identifier 21 as shown, or may be generating feed 132 of a camera image 180b of a real world 80 including medical tool 20 and/or tool identifier 21 as shown.

In practice, medical tool recognition module 41 is configured in accordance with object recognition techniques for identifying medical tool 20 and/or tool identifier 21 within camera image 180b of real world 80 including medical tool 20 and/or tool identifier 21 as known in the art of the present disclosure.

In one embodiment, medical tool recognition module 41 is configured in accordance with object recognition techniques based on matching, learning, or pattern recognition algorithms using appearance-based, model-based or feature-based techniques for identifying a specific object in a digital image or video. Such techniques may be incorporate feature extraction and machine learning models, deep learning models (e.g., convolutional neural networks), bag-of-word models, gradient-based and derivative-based matching approaches, template matching and/or image segmentation and blob analysis.

In response to a recognition of medical tool 20 and/or tool identifier 21 within camera image 180b of real world 80, a stage S74 of flowchart 70 encompasses each medical device trigger module 42 triggering a medical procedure action by primary augmented reality device 30, secondary augmented reality device 130 (if applicable) and/or one or more medical devices 50.

In practice, each medical device trigger module 42 is configured in accordance with basic programming techniques for commanding a configuration, a signal enabling/disabling (unmodulated and modulated) and/or a function calling of primary augmented reality device 30, secondary augmented reality device 130 (if applicable) and/or one or more medical devices 50.

Figure 5A:
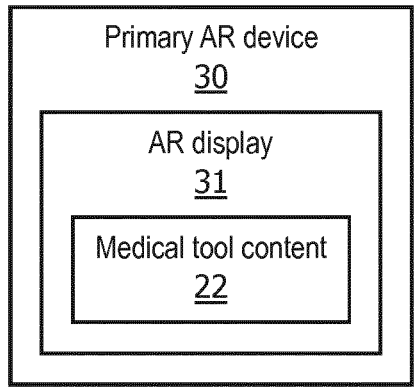
FIGS. 5A-5D illustrate exemplary embodiments of a display of medical tool content and a medical tool hologram in accordance with the inventive principles of the present disclosure.

In one embodiment, as exemplary shown in FIG. 5A, a medical drive trigger module 42 may issue a command 142a for primary augmented reality device 30 to display medical tool content 22 as previously stored within primary augmented reality device 30, or as communicated to primary augmented reality device 30 via module 42 or another content source.

In practice, medical tool content 22 may be any type of content related to medical tool 20. Examples of medical tool content 22 include:
1. an overlay of medical tool on AR display 31;
2. an input feed of the medical tool 20;
3. a description of the medical tool 20;
4. instructions for operating the medical tool 20;
5. any warnings associated with the medical tool 20 (e.g., an expiration warning, a recalled warning, an imaging compatibility/incompatibility and a patient type recommendations);
6. conditions of common and special use cases of medical tool 20, particularly historical cases of medical tool 20 as related to the current medical procedure;
7. links to search results about the medical tool 20 for planning purposes (e.g., publications, articles, videos, etc.); and
8. a display of a price of medical tool 20 and indication if a less expensive similar medical tool is available for the current procedure.

For these examples, medical drive trigger module 42 further controls a logging of the use of medical tool 20 during the current medical procedure for inventory management purposes.

Additionally, medical drive trigger module 42 may provide auditory feedback informative of medical tool content 22.

Figure 5B:
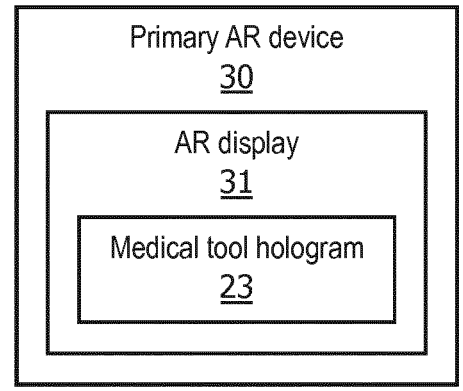
Figure 5C:
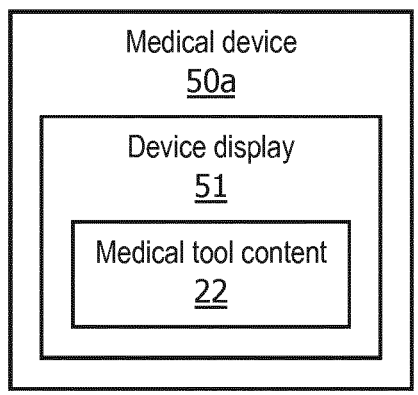

Concurrently or alternatively, a medical drive trigger module 42 may issue a command 142b for secondary augmented reality device 130 to display medical tool content 22 as previously stored within secondary augmented reality device 130, or as communicated to secondary augmented reality device 130 via module 42 or another content source, and/or as shown in FIG. 5C, medical drive trigger module 42 may issue a command 142c for a medical device 50 to display medical tool content 22 via a device display 51 as previously stored within the medical device 50, or as communicated to the medical device 50 via module 42 or another content source.

In a second embodiment, as exemplary shown in FIG. 5B, a medical drive trigger module 42 may issue a command 142a for primary augmented reality device 30 to display a medical tool hologram 23 as previously stored within primary augmented reality device 30, or to load medical tool hologram 23 from module 42 or another hologram source for display. This provides for a virtual testing of a positioning of medical tool 20 relative to a patient anatomy.

Figure 5D:
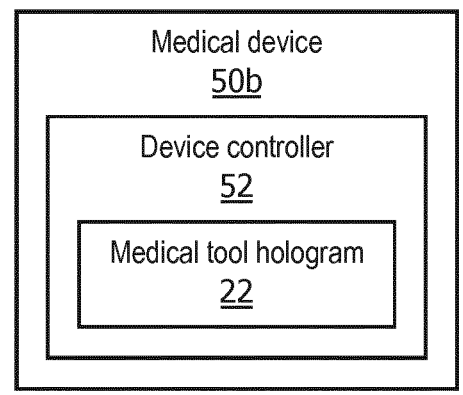

Concurrently or alternatively, a medical drive trigger module 42 may issue a command 142b for secondary augmented reality device 130 to display medical tool hologram 23 as previously stored within secondary augmented reality device 130, or to load medical tool hologram 23 from module 42 or another hologram source for display, and/or as shown in FIG. 5D, medical drive trigger module 42 may issue a command 142c for a medical device 50 to display a medical tool hologram 23 via a device display 51 as previously stored within the medical device 50, or to load medical tool hologram 23 from module 42 or another hologram source to a device controller 52 for display.

Figure 6A:
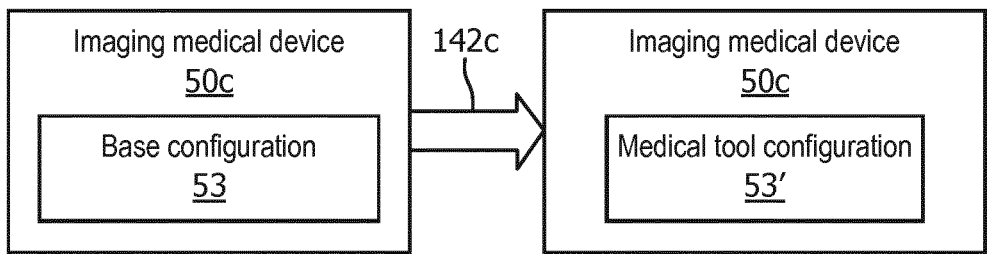
FIGS. 6A and 6B illustrate exemplary actions of an imaging medical device in accordance with the inventive principles of the present disclosure.

In a third embodiment, a medical drive trigger module 42 may issue a command 142c to configure a medical device 50. For example, as shown in FIG. 6A, an imaging medical device 51c may be reconfigured from a base configuration 53 to a configuration 53' including a specific protocol suitable for medical tool 20. By further example, medical tool 20 in the form of a balloon catheter may trigger a DSA setting of an X-ray imaging apparatus by automatically setting the protocol or prompting a user to accept a suggested protocol.

Figure 6B:
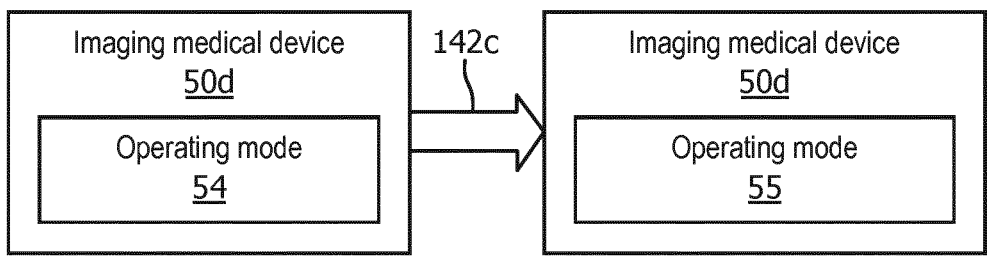

In a fourth embodiment, a medical drive trigger module 42 may issue a command 142c to switch a medical device 50 from one operating mode to another operating mode. For example, as shown in FIG. 6B, an imaging medical device 51d may be switched from an operating mode 54 to an operating mode 55. For this example, operating mode 54 may encompass an X-ray imaging of a navigation and treatment of a catheter relative to a patient anatomy whereby a recognition of a vascular closure tool via primary AR device 30 indicates a conclusion of operating mode 54, which triggers a switch to operating mode 55 including a lowering of an X-ray patient table, a movement of an X-ray C-arm to a parking position and a disabling of the X-ray emitter to facilitate deployment of the vascular closure tool.

Subsequent to the medical device triggering of stage S74, flowchart 700 may be terminated or returned to stage S72 for a recognition of additional medical tool(s) 20 utilized during the medical procedure.

Referring back to FIG. 1, in practice, modules 41 and 42 are pre-configured to trigger an appropriate medical procedure action based on a recognition of medical tool 20 and/or tool identifier 21 within a cameral image of a real world as previously described in the present disclosure. Alternatively, an operator of system 10 may configure modules 41 and 42 to a trigger of an appropriate medical procedure action based on a recognition of medical tool 20 and/or tool identifier 21 within a cameral image of a real world as previously described in the present disclosure.

In one embodiment, trigger action controller 40 may incorporate a user interface providing for a programming of rules, graphically or textually, of modules 41 and 42 for delineating an object recognition of medical tool 20 and/or tool identifier 21 within a cameral image of a real world and an appropriate medical procedure action triggered by such an object recognition.

In a second embodiment, trigger action controller 40 may incorporate an application as known in the art of the present disclosure for recognizing a particular medical tool 20 for a first time whereby module 41 may be configured to thereafter be able to recognize the medical device 20 and module 42 may be configured to trigger the appropriate medical procedure action triggered by such a recognition.

In a third embodiment, trigger action controller 40 may be configured to store activities during executions of a particular medical procedure whereby one or more training models may be developed based on inputs from primary AR device 30, operator inputs and/or any procedural protocols and/or information related to medical tool 20 and/or medical device (s) 50. During a current execution of the medical procedure, the historical data of the training models facilitate a prediction by a module 42 of an appropriate medical procedure action to trigger upon a recognition of medical tool 20 and/or tool identifier 21 within a cameral image of a real world and an appropriate medical procedure action triggered by such an object recognition.

Referring to FIGS. 1-6, those having ordinary skill in the art of the present disclosure will appreciate numerous benefits of the inventions of the present disclosure including, but not limited to, on an object recognition of a medical tool by an augmented reality device serving as a trigger for an action by the augmented reality device, a medical device and/or an additional augmented reality device to thereby minimize any interruption to the workflow of a medical procedure. Those having ordinary skill in the art will further appreciate the applicability of the inventions of the present disclosure to non-medical systems, methods, tools and devices.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An augmented reality trigger system comprising:
   a primary augmented reality device configured to generate a camera image of a real world; and
   a trigger action controller configured to:
      receive, from the primary augmented reality device, the camera image of the real world including a medical tool, identify the medical tool within the camera image as a particular medical tool, and trigger a medical procedure action, by at least one of the primary augmented reality device and a medical device configured to image a medical procedure, in response to the identification of the medical tool as the particular medical tool, wherein the triggered medical procedure action includes triggering the medical device to set an operational mode related to the medical tool for imaging the medical tool.

2. The augmented reality trigger system of claim 1, wherein the trigger action controller is configured to identify the medical tool as the particular medical tool based on a shape of the medical tool within the camera image.

3. The augmented reality trigger system of claim 1, wherein the trigger action controller is configured to identify the medical tool as the particular medical tool based on a tool identifier associated with the medical tool, and the tool identifier includes at least one of:

a tool label;
a custom marker attached to the medical tool; and
a custom marker unattached to the medical tool.

4. The augmented reality trigger system of claim 1, wherein the trigger action controller is further configured to at least one of:

trigger a display by the primary augmented reality device of content related to the medical tool; and
trigger a display by the primary augmented reality device of a holographic model of the medical tool.

5. The augmented reality trigger system of claim 4, wherein the content related to the medical tool includes at least one of:

an overlay of the medical tool of a virtual screen of the primary augmented reality device;
an input feed of the medical tool;
a description of the medical tool;
instructions for operating the medical tool;
cases involving the use of at least one of the medical tool and additional medical tool similar to the medical tool; and
one or more warnings associated with the medical tool.

6. The augmented reality trigger system of claim 1, wherein the medical device is configured to display a real world image of the medical tool; and wherein the trigger action controller is further configured to at least one of:

trigger a display by the medical device of content related to the medical tool; and
trigger a display by the medical device of a holographic model of the medical tool.

7. The augmented reality trigger system of claim 6, wherein the content related to the medical tool includes at least one of:

an input feed of the medical tool;
a description of the medical tool;
instructions for operating the medical tool;
cases involving the use of at least one of the medical tool and additional medical tool similar to the medical tool; and
one or more warnings associated with the medical tool.

8. The augmented reality trigger system of claim 1, further comprising:

a secondary augmented reality device; and
wherein the trigger action controller is further configured to:

triggering a medical procedure action by at least one of the primary augmented reality device, the medical device, and the secondary augmented reality device in response to the identification of the medical tool as the particular medical tool.

9. The augmented reality trigger system of claim 1, wherein the medical tool is one of a guidewire, a catheter, a valve, or a stent.

10. A trigger action controller comprising:

at least one processor configured to:

receive, from a primary augmented reality device, a camera image of a real world including a medical tool;
identify the medical tool within the camera image as a particular medical tool; and
trigger a medical procedure action, by at least one of the primary augmented reality device and a medical device configured to image a medical procedure, in response to the identification of the medical tool as the particular medical tool,
wherein the at least one processor is further configured to trigger the medical device to set an operational mode related to the medical tool for imaging the medical tool.

11. The trigger action controller of claim 10, wherein the at least one processor is further configured to at least one of:

trigger a display by the primary augmented reality device of content related to the medical tool; and
trigger a display by the primary augmented reality device of a holographic model of the medical tool.

12. The trigger action controller of claim 10, wherein the medical device is configured to display a real world image of the medical tool; and
wherein the at least one processor is further configured to at least one of:

trigger a display by the medical device of content related to the medical tool; and
trigger a display by the medical device of a holographic model of the medical tool.

13. The trigger action controller of claim 10, wherein the at least one processor is further configured to:

trigger an action by at least one of the primary augmented reality device, the medical device, and a secondary augmented reality device in response to the identification of the medical tool as the particular medical tool.

14. The trigger action controller of claim 10, wherein the at least one processor is configured to identify the medical tool as the particular medical tool based on a tool identifier associated with the medical tool, and the tool identifier includes at least one of:

a tool label;
a shape of the medical tool;
a custom marker attached to the medical tool; and
a custom marker unattached to the medical tool.

15. An augmented reality trigger method comprising:

receiving, by a trigger action controller from a primary augmented reality device, a camera image of a real world including a medical tool;
identify the medical tool within the camera image as a particular medical tool; and
triggering, by the trigger action controller, a medical procedure action, by at least one of the primary augmented reality device and a medical device configured to image a medical procedure, in response to the identification of the medical tool as the particular medical tool, wherein the triggering of the medical procedure action includes triggering the medical device to set an operational mode related to the medical tool for imaging the medical tool.

16. The augmented reality trigger method of claim 15, wherein triggering the medical procedure action includes at least one of:
   triggering, by the trigger action controller, a display by the primary augmented reality device of content related to the medical tool; and
   triggering, by the trigger action controller, a display by the primary augmented reality device of a holographic model of the medical tool.

17. The augmented reality trigger method of claim 15, wherein the medical device is configured to display a real world image of the medical tool; and
   wherein triggering the medical procedure action by the medical device includes at least one of:
      triggering, by the trigger action controller, a display by the medical device of content related to the medical tool; and
      triggering, by the trigger action controller, a display by the medical device of a holographic model of the medical tool.

18. The augmented reality trigger method of claim 15, further comprising:
   triggering an action by at least one of the primary augmented reality device, the medical device, and a secondary augmented reality device in response to the identification of the medical tool as the particular medical tool.

19. The augmented reality trigger method of claim 15, wherein identification of the medical tool as the particular medical tool is based on a tool identifier associated with the medical tool, and the tool identifier includes at least one of:
   a tool label;
   a shape of the medical tool;
   a custom marker attached to the medical tool; and
   a custom marker unattached to the medical tool.

* * * * *